US011366050B1

United States Patent
Litvinov et al.

(10) Patent No.: US 11,366,050 B1
(45) Date of Patent: Jun. 21, 2022

(54) ULTRA-SENSITIVE VOLUMETRIC MAGNETIC PARTICLE DETECTOR

(71) Applicants: Dmitri Litvinov, Friendswood, TX (US); Long Van Chang, Pearland, TX (US); Mohammad Khodadadi, Houston, TX (US); Richard Coale Willson, Houston, TX (US)

(72) Inventors: Dmitri Litvinov, Friendswood, TX (US); Long Van Chang, Pearland, TX (US); Mohammad Khodadadi, Houston, TX (US); Richard Coale Willson, Houston, TX (US)

( * ) Notice: Subject to any disclaimer, the term of this patent is extended or adjusted under 35 U.S.C. 154(b) by 338 days.

(21) Appl. No.: 16/775,975

(22) Filed: Jan. 29, 2020

Related U.S. Application Data (60) Provisional application No. 62/798,056, filed on Jan. 29, 2019.

(51) Int. Cl.
*G01N 15/10* (2006.01)
*G01N 33/543* (2006.01)
*G01N 33/487* (2006.01)
*G01N 15/00* (2006.01)

(52) U.S. Cl.
CPC ....... *G01N 15/1031* (2013.01); *G01N 33/487* (2013.01); *G01N 33/54366* (2013.01); *G01N 2015/0065* (2013.01)

(58) Field of Classification Search
CPC ............. G01N 15/1031; G01N 33/487; G01N 33/54366; G01N 2015/0065
See application file for complete search history.

(56) References Cited

U.S. PATENT DOCUMENTS

| | | |
|---|---|---|
| 4,277,750 A | 7/1981 | Bonnet |
| 7,732,220 B2 | 6/2010 | Nikitin |
| 7,785,902 B2 | 8/2010 | Nikitin |
| 7,910,063 B2 | 3/2011 | Kriz |
| 8,026,716 B2 | 9/2011 | Makiranta |
| 2004/0150396 A1 | 8/2004 | Simmonds |

OTHER PUBLICATIONS

Rabehi et al. "Magnetic Detection Structure for Lab-on-Chip Applications Based on the Frequency Mixing Technique". Sensors (Basel). May 29, 2018;18(6):1747. doi: 10.3390/s18061747. PMID: 29844260; PMCID: PMC6021809. (Year: 2018).*

(Continued)

*Primary Examiner* — Jennifer Wecker
*Assistant Examiner* — Jonathan Bortoli (57) ABSTRACT

The invention is a novel and non-obvious design and implementation of an inductive sensor for quantifying magnetic particles. The invention parts way from the conventional methods of using wounded coils to a design that is compatible with an integrated circuit (IC) chip fabrication processes and/or printed circuit board (PCB) manufacturing. The increased accuracy from these fabrication methods provides a significant improvement to sensor sensitivity. In addition, the design of the inductive sensor enables easy integration with lateral flow assay (LFA) technology. The sensor can be applied to detect and quantify molecules to provide information on health, hazard or safety.

19 Claims, 6 Drawing Sheets

An illustrative embodiment of a sensor showing the (a) inside and the (b) outside (56) References Cited

OTHER PUBLICATIONS

Meyer et al. "CRP determination based on a novel magnetic biosensor. Biosens Bioelectron" Jan. 15, 2007;22(6):973-9. doi: 10.1016/j.bios.2006.04.001. PMID: 16766177. (Year: 2007).*

Nanotechnology 15 (2004) 457-466 PII: S0957-4484(04)69059-3, A novel and rapid method for quantification of magnetic nanoparticle-cell interactions using a desktop susceptometer, Valter Strom, Kjell Hultenby, Cordula Gruttner, Joachim Teller, Bo Xu and Jan Holgersson.

Proceedings of the 28th IEEE EMBS Annual International Conference New York City, USA, Aug. 30-Sep. 3, 2006, Electrical properties of electrodes in implantation conditions, J. Mäkiranta, J. Verho, J. Lekkala and N. Matintupa.

* cited by examiner

FIG 1: An illustrative embodiment of a sensor showing the (a) inside and the (b) outside FIG 2: An illustrative embodiment of a sensor with a lateral flow assay FIG 3: An illustrative embodiment of a sensor with a channel FIG 4: An embodiment of a sensor manufactured using PCB manufacturing technology with (a) SMA connectors and (b) edge connectors FIG 5: (a) A comparison of the sensor signal (left) and the magnetic moment (right) are used to quantify the number of magnetic nanoparticles immobilized in the test line of an LFA with various concentrations of hCG pregnancy hormone. (b) A comparison of the sensor signal (left) and the number of magnetic particles (right) in the test line.

FIG 6: The ratio of the number of hCG molecules in the sample to the number of magnetic particles (Adembead) reporters measured in the test line increases monotonically with increasing hCG concentration.

ULTRA-SENSITIVE VOLUMETRIC MAGNETIC PARTICLE DETECTOR

CROSS-REFERENCE TO RELATED APPLICATIONS

This application claims the benefit of the U.S. Provisional Patent Application No. 62/798,056 filed on Jan. 29, 2019, which is incorporated herein by reference.

BACKGROUND OF THE INVENTION

Field of the Invention

This invention relates to a magnetic sensor designed for the detection of biological and chemical targets for biomedical, food safety, civil defense, and military defense applications. More particularly, to an extremely sensitive, portable, accessible, and easily manufacturable sensor system.

Description of the Prior Art

The following is a tabulation of some prior art that presently appears relevant:

U.S. Pats.

| U.S. Pat. No. | Kind Code | Issue Date | Patentee |
|---|---|---|---|
| 7,785,902 | B2 | 2010 Aug. 31 | Nikitin |
| 7,910,063 | B2 | 2011 Mar. 22 | Kriz |
| 8,026,716 | B2 | 2011 Sep. 27 | Makiranta |
| 7,732,220 | B2 | 2010 Jun. 8 | Nikitin |
| 4,277,750 | B2 | 1981 Jul. 7 | Bonnet |

U.S. Pat. application Publications

| Publication No. | Kind Code | Publication Date | App or Patentee |
|---|---|---|---|
| 20040150396 | A1 | 2004 Aug. 5 | Simmonds et al. |

Nonpatent Literature Documents

Valter Strom, Kjell Hultenby, Cordula Gruttner, Joachim Teller, Bo Xu, and Jan Holgersson, "A novel and rapid method for quantification of magnetic nanoparticle-cell interactions using a desktop susceptometer," Nanotechnology 15 (2004) 457-466 PII S0957-4484(04)69059-3.

J. Makiranta, J. Verho, J. Lekkala, and N. Matintupa, "Electrical properties of electrodes in implantation conditions," Proceedings of the 28th IEEE EMBS Annual International Conference New York City, USA, Aug. 30-Sep. 3, 2006

Clinical chemistry is a prevalent technology enabling doctors to parameterize diagnostics before, during, and after treatment. Concentrations of specific biomolecules may be quantified using methods mimicking biological processes to generate detectable signals. ELISA, a popular diagnostic platform, is performed on microtiter plates with 96 or more sample wells involving labor-intensive steps, taking several hours, and having a high recurrent cost.

A popular molecular diagnostic platform is the lateral-flow assay (LFA), the technology underlying the home pregnancy test. Various LFA implementations have been extensively explored for applications in rapid and inexpensive point-of-care medical diagnostics due to its low cost, ease of use, and sensitivity sufficient for many applications. A typical LFA reading is based on observing a color change of the test line due to the selective accumulation of reporters in the test line. Visual information is limited to the reporters near the surface of the LFA strip, with limited or no ability to capture the majority of the signal hidden in the volume of the test line. Analyte quantification is challenging as a result of variations in lighting, sample volume, and the operator's visual acuity. Despite numerous advancements in colorimetric reporters such as gold nanocages, nanotubes, carbon nanoparticles, and cellulose nanobeads, among others, the sensitivity, signal range, and quantifiability of colorimetric reporters based LFAs remain a challenge. The use of other optical reporters such as fluorescent dyes or luminescent nanoparticles faces various challenges due to reagent complexity, cost, and reader complexity. Many tests are not viable in the LFA platform because sensitivity is lacking and/or quantifiability is not available.

By replacing the colorimetric reporters used in an LFA with magnetic particle reporters such as superparamagnetic nanoparticles immuno-captured in the volume of the test line, it is possible to improve the sensitivity and/or provide quantifiability. Magnetic reporters provide a number of unique advantages over optical reporters: (1) magnetic fields do not interact with biological materials, so magnetic field-based detection is immune to signal degradation and distortion inherent to optical detection; (2) magnetic fields are not affected by LFA media, so every magnetic reporter within the test line volume contributes to detection; and (3) the properties of magnetic reporters can be tuned to match the biomarkers to optimize immobilization efficiency and detection. The detection of the magnetic particles immobilized in an LFA media can be accomplished using inductive magnetic sensors.

The fundamental physics of induction sensors for detecting magnetic material is well established. It was used in several generations of magnetic hard drives and tape recorders where inductive pickup coils were used to measure magnetic data from a hard disk drive or a magnetic tape. Inductive sensing is also used in ac susceptometry for measuring the paramagnetic, diamagnetic or ferromagnetic susceptibility of magnetic materials. AC susceptometry have been adapted for use in biodiagnostic applications and commercial systems are available as shown in the table below:

| | Nanorian CryoBIND | Imego DynoMag | Magnisense MIAtek |
|---|---|---|---|
| Sensitivity | $10^{-9}$ emu | $10^{-8}$ emu | $10^{-8}$ emu |
| Sample Volume | 10 uL | 200 uL | 25 uL |
| Frequency | 1 Hz to 100 kHz | 1 Hz to 250 kHz | 10 Hz to 100 kHz |

AC susceptometer systems typically use hand wounded coils for the inductive sensor and often a pair of hand-wound coils are connected together in opposition to provide a differential measurement (U.S. Pat. No. 4,277,750 and publication by Strom 2004). A differential measurement can provide a significant improvement to sensitivity, but it requires a pair of symmetric coils which is difficult to manufacture. After manufacture, the coils may become more asymmetric from environmental effects such as heating, drift, or vibration. To compensate for imbalances that arise from asymmetries in the coil pair, inventors developed a two-frequency method (U.S. Pat. Nos. 7,732,220 and 7,785,902) or the drift compensation method (U.S. Pat. No. 7,910,063). Another limiting problem with a hand-wound coil is that it puts restrictions on the sample format which increases cost.

More symmetric coils can be produced using more precise manufacturing technology such as integrated circuit manufacturing or printed circuit manufacturing. Magnasense (U.S. Pat. No. 8,026,716) made an AC susceptometer as a pair of planar spiral inductors using printed circuit board manufacturing technology. The sensing performance of a planar inductor varies greatly depending on the position of the magnetic particle reporter on the sensor. For example, in a 3 loop spiral inductor, a magnetic particle at the center will be picked up by all three loops, but a magnetic particle near the edge of the sensor will only be picked up by one loop (U.S. Patent application publication 20040150396 and publication by Makiranta 2006).

SUMMARY OF THE INVENTION

Our invention further improves the induction sensor for biodiagnostic application by using integrated circuit manufacturing and/or printed circuit board manufacturing to make inductive sensors that wrap around the test volume of a diagnostic test such as a lateral flow assay. The advantages of this invention are: a) higher sensitivity achieved via better magnetic sample flux collection efficiency, higher operating frequencies, and the ability to fabricate more symmetric sample and reference inductor pairs, and b) readily integrate with lateral flow assay and/or microfluidic technologies with minimal modification to the technology. The design of an induction sensor for quantifying magnetic particles and a method of manufacturing such sensors are discussed further herein.

The invention is a novel and non-obvious design and implementation of an inductive sensor for quantifying magnetic particles for use in biosensing and/or chemical sensing applications. The invention parts way from the conventional methods of using wounded coils to a design that is compatible with an integrated circuit (IC) chip fabrication processes and/or printed circuit board (PCB) manufacturing. The increased accuracy from these fabrication methods provides a significant improvement to sensor sensitivity. The design of the inductive sensor enables easy integration with lateral flow assay (LFA) technology.

The invention comprises an excitation source, a sample sensor, and a reference sensor. The excitation source generates a time-varying magnetic field [alternating current (ac), a train of pulses, individual pulse, etc.] in the sample volume of the sample sensor and the reference volume of the reference sensor. The excitation source, sample sensor, and reference sensor are arranged such that the spatial distribution and magnitude of the excitation magnetic field are identical or nearly identical in the sample and reference volumes. The sample sensor and reference sensor form a sensor pair when they are electrically connected in series and wound in opposition such that a net induced voltage across the sensor pair is zero when the quantity of magnetic material inside the sample volume and the reference volume are identical. When the quantity of magnetic material inside the sample volume and reference volume is different, a net non-zero induced voltage will be produced by the sensor pair that is proportional to the disparity in the quantity of the magnetic material within the volumes.

The invention can be integrated with biomolecular and/or chemical recognition technologies to be applied to detect cancer, infectious diseases, biological threats, food pathogens, and/or other situations that require identification and quantification of biomolecular or chemical species. Analytes such as proteins, DNA, RNA, cells, spores, viruses, exosomes, metabolites, toxins, drugs, or contaminants can be detected with molecular recognition agents such as nucleic acids and nucleic acid analogs, antibodies and antibody fragments and analogs, aptamers, peptides, lectins, and receptors. Competition for molecular recognition agents can be established between analytes and immobilized analytes, or analyte analogs. In biomedical applications, disease biomarkers can be labeled with magnetic particles and specifically immobilized within the sample volume. The presence of magnetic particles specifically immobilized within the sample volume will generate an induced voltage in the sample sensor that is proportional to the quantity of magnetic particles. In the absence of magnetic particles within the reference volume, the induced voltage in the reference sensor will be different from the induced voltage in the sample volume. The difference between induced voltages across the sensor pair is proportional to the disparity in the quantity of magnetic particles in the sample volume and the reference volume. In practice, the reference volume and the sample volume will also contain a certain quantity of magnetic particles that are non-specifically bound. The difference between induced voltages across the sample sensor and the reference sensor pair will provide information about the specifically bound magnetic particles. This net induced voltage can be calibrated to quantify the number of molecules used to specifically bound the magnetic particles to the sample volume. Therefore, quantifying the magnetic particles is equivalent to quantifying a specific molecule in a biological sample. The quantification of magnetic particles can be used to determine the concentration and/or presence/absence of a specific biomolecule in the sample. In this embodiment, the invention is applied to interpret an LFA test by providing a quantification or qualification of the test line and a validation of the control line. Sensors of this design also can be used to detect and quantitate magnetic materials bound to a solid in other formats such as flow-through or dipstick, or free in solution or suspension, or aggregates or particles bound to particles or cells. Sample preparation means including filters, adsorbents, density separation agents, and centrifugal forces can be used to prepare samples for analysis, and/or incorporated into the testing apparatus. Blood filters and conjugate release pads may optionally be incorporated into the lateral-flow assay. As a non-limiting example, when the invention is combined with a pregnancy test, the induced voltage from the test line sensor pair quantifies the concentration of the hCG pregnancy hormone to determine pregnancy and the induced voltage from the control line sensor pair quantifies the concentration of magnetic material to validate the test.

In one embodiment, the excitation source and sensors are made on two separate pieces of the printed circuit board (PCB) using PCB manufacturing technology. An LFA is aligned to the first PCB such that the test line on the LFA is aligned to the sample sensor and a null line is aligned to the reference sensor. The test line is the sample volume and the null line is the reference volume. The null line is a blank volume on the LFA with no specific biochemistry to capture magnetic particles. In addition, the control line of the LFA can be aligned to the second pair of sensors on the first PCB where the control line is the sample volume and a second null line is the reference volume. The second PCB is then assembled and electrically connected to the first PCB to complete the assembly of the excitation source and the sensors. The advantages of this approach are: a) the sensor pair wraps around the sensing volume and reference volumes on the LFA, providing efficient detection of the quantity of magnetic particles in the volumes, b) the excitation source is integrated with the sensor, providing a more uniform time-varying magnetic field with frequencies up to 2 GHz, and c) the LFA can be easily assembled into the device before completely assembling the sensors.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Figure 1:
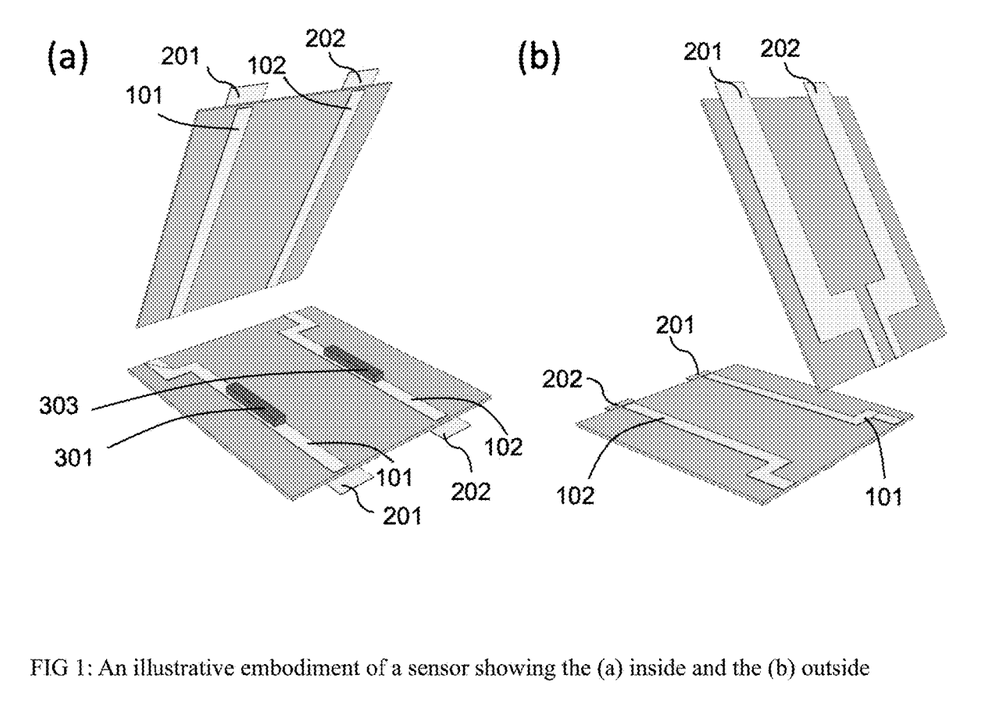
FIG. 1A shows a view of the inside of the sensor
FIG. 1B shows a view of the outside of the sensor

FIG. 1A and FIG. 1B shows an embodiment of the sensor. A set of sensing conductors [101] sandwiches a detection volume [301]. A set of sensing conductors [102] sandwiches a second detection volume [303]. A set of excitation conductors [201] sandwiches a set of sensing conductors [101] and [102]. A set of excitation conductors [202] sandwiches a set of sensor conductors [102].

The set of excitation conductors [201] provides a time-varying magnetic field to the set of sensing conductor [101]. The set of sensing conductor [101] provides an induced voltage proportional to the quantity of magnetic material in the detection volume [301]. The magnetic material in the detection volume [301] provides amplification to the induced voltage, thereby a larger quantity of magnetic material will proportionally increase the magnitude of the induced signal. Similarly, the set of excitation conductors [202] provides a time-varying magnetic field to the set of sensing conductor [102]. The set of sensing conductor [102] provides an induced voltage proportional to the quantity of magnetic material in the detection volume [302].

The time-varying magnetic fields provided by excitation conductors [201], and excitation conductors [202], are approximately the same. The time-varying magnetic field can have a frequency in the range of 10 kHz to 2 GHz. The time-varying magnetic field can be generated using a single frequency waveform, an arbitrary waveform, or a pulse train.

The induced voltage provided by a sensing conductor is comprised of: a) induction from the time-varying magnetic field provided by the excitation conductor, b) induction from the time-varying magnetic field provided by the magnetic material, and c) other sources. As a non-limiting example, other sources can be a time-varying magnetic field provided by the environment.

The set of sensing conductor [101] is connected to the set of sensing conductor [102] forming a sensor pair [101-102] and the net induced voltage is zero when the quantity of magnetic material in detection volume [301] is equal to the quantity of magnetic material in detection volume [302]. In addition, a non-zero net induced voltage provided by the sensor pair [101-102] is proportional to the disparity in the quantity of magnetic material in detection volume [301] and [302]. Pairing the sensing conductors this way provides increased sensitivity. As a non-limiting example, the detection volume [301] is filled with magnetic material and non-magnetic material and the detection volume [302] is filled with only non-magnetic material. The sensor pair will provide a net induced voltage that is proportional to the quantity of magnetic material minus the contribution from non-magnetic material and the environment.

As a non-limiting example, the magnetic material in a detection volume is a magnetic particle with superparamagnetic properties and a diameter smaller than 10 micrometers. The magnetic particle may be a magnetic nanoparticle, a magnetic nanorod, a polymer bead embedded with magnetic nanoparticles, or any suitable material with magnetic properties. As a non-limiting example, the magnetic material is a superparamagnetic iron oxide nanoparticle embedded in a polymer matrix with a diameter of smaller than 10 micrometers.

Figure 2:
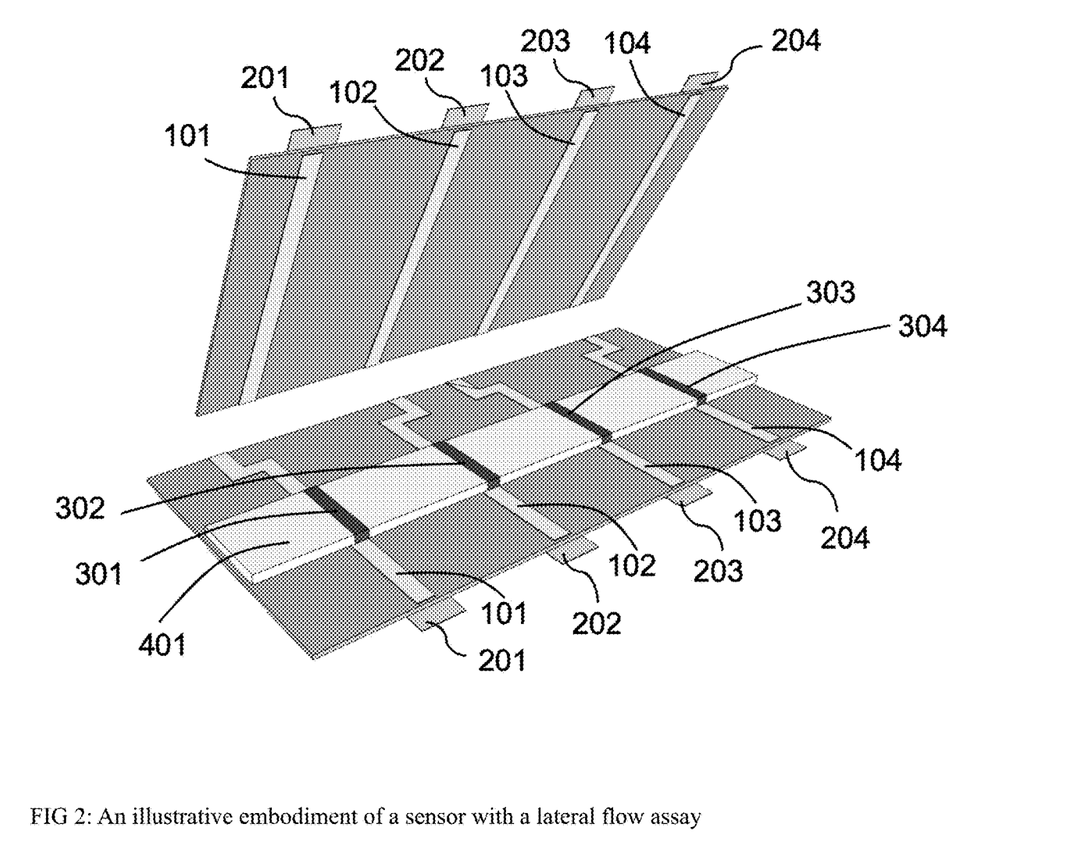
FIG. 2 shows a sensor with a lateral flow assay

FIG. 2 shows an illustrative embodiment of a sensor integrated with an LFA [401]. The sensor in FIG. 2 to provide a total of 4 sensing conductors [101 to 104], 4 excitation conductors [201 to 204], and 4 detection volumes [301 to 304]. An LFA membrane [401] provides a test line [301], a null line [302], a control line [303] and a second null line [304]. The test line [301] coincide with the detection volume [301]. Similarly, the null line [302], control line [303] and second null line [304] coincide with the detection volumes [302], [303] and [304] respectively.

The LFA uses magnetic particles as reporters. As the magnetic particles and the sample flow through the LFA, the magnetic particles and target molecules in the sample interact with the delivery medium [401], the test line [301] and the control line [303]. The delivery medium [401] is an LFA membrane. The magnetic particles and target molecules should flow pass the LFA membrane [401]. Magnetic particles that get stuck in the LFA membrane is unintentional and provides an induced signal at the null line [302] and [304]. The magnetic particles should be immobilized in the test line [301] only if the target molecule is present in the sample. The magnetic particle should always be immobilized in the control line [303].

The sensing conductor [101] and [102] are connected to form a sample sensor pair [101-102] so that the net induced voltage is proportional to the difference in the quantity of magnetic particles in the test line [301] and the null line [302]. The test line [301] is designed to immobilize magnetic particles only if the target molecule is in the sample. The net induced voltage provided by the sample sensor pair [101-102] corresponds to the quantity of target molecules in the sample.

The sensing conductor [103] and [104] are connected to form a control sensor pair [103-104] so that the net induced voltage is proportional to the difference in the quantity of magnetic particles in the control line [303] and null line [304]. The control line [303] is designed to immobilize the magnetic particles no matter what molecules are in the sample. The net induced voltage provided by the control sensor pair [103-104] is used to validate the LFA.

The sensor integrated with an LFA can be applied to provide information on health, hazard or safety. As a non-limiting example, an LFA designed to test for pregnancy can be integrated with the sensor. The net induced voltage provided by the sample sensor pair [101-102] corresponds to the quantity of pregnancy molecular marker in the test line [301]. The net induced voltage provided by the control sensor pair [103-104] corresponds to the quantity of magnetic particles in the control line [303]. A sufficient quantity of magnetic particles in the control line [303] validates the test. As a non-limiting example, an LFA designed to test for prostate cancer can be integrated with the sensor. The net induced voltage provided by the sample sensor pair [101-102] corresponds to the quantity of prostate-specific antigen in the test line [301]. The net induced voltage provided by the control sensor pair [103-104] corresponds to the quantity of magnetic particles in the control line [303]. A sufficient quantity of magnetic particles in the control line [303] validates the test.

The sensor can have additional sensing conductors, detection volumes and excitation conductors. As a non-limiting example, a sensor providing 6 sensing conductors, 6 detection volumes and 6 excitation conductors can be integrated with an LFA. The LFA may provide a test line, a reference line, and a control line. As a non-limiting example, a reference line may immobilize magnetic particles using a different target molecule, a competitive molecule, or a passivated volume of the LFA. The sensor providing additional sensing conductors, detection volume and excitation conductors enable compatibility with more complex tests. As a non-limiting example, a single test can quantify more than one target molecule from a sample.

Figure 3:
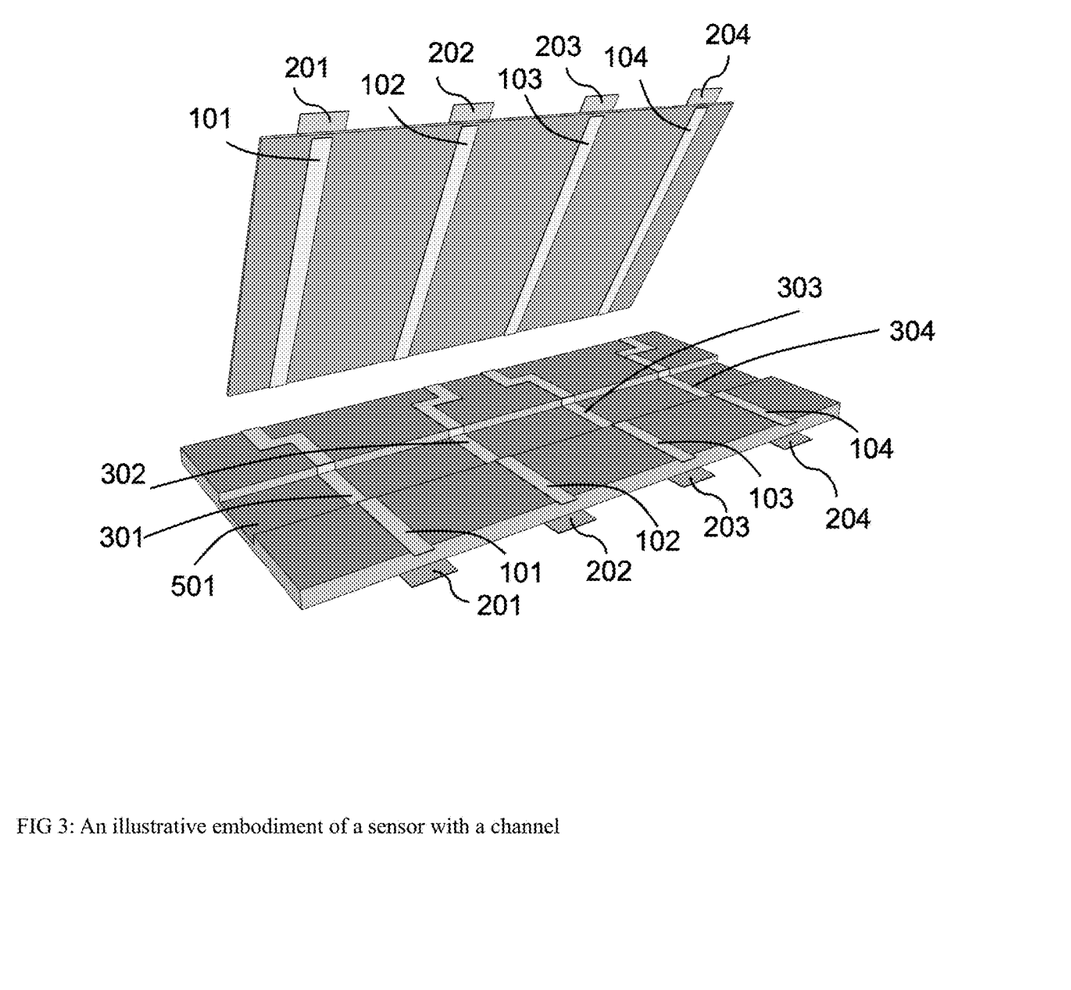
FIG. 3 shows a sensor with a channel

FIG. 3 shows an illustrative embodiment of a sensor with a channel [501]. The detection volume [301] is the volume inside the channel sandwiched between the sensing conductor [101]. Similarly, detection volumes [302], [303], and [304] are the volume inside the channel sandwiched between sensing conductors [102], [103], and [104] respectively. An LFA can be inserted inside the channel [501] to produce a sensor integrated with an LFA. The channel [501] provides the option to integrate microfluidics as a medium for delivery.

As a non-limiting example, the channel [501] is a microfluidic channel that pumps a solution comprising magnetic particles and a sample containing a target molecule. The detection volume [301] comprises of a monolith that is prepared to immobilize magnetic particles when the target molecule is present in the sample. The detection volume [302] serves as a reference of the environment. The net induced voltage from the sample sensor pair [101-102] corresponds to the number of target molecules in the detection volume [301]. The detection volume [303] comprises of a monolith that is prepared to immobilize magnetic particles. The detection volume [304] serves as a reference of the environment. The net induced voltage from the control sensor pair [103-104] is proportional to the quantity of magnetic particles immobilized in detection volume [303].

A porous media is used in a detection volume to provide a large surface area to interact with magnetic particles and target molecules. A porous media can be a monolith, a nitrocellulose membrane, a glass fiber membrane, or a porous bead.

As a non-limiting example, the channel [501] is a microfluidic channel that pumps a solution comprising magnetic particles, a sample containing a target molecule, a larger porous bead, and a smaller porous bead. The larger porous bead is designed to immobilize magnetic particles when a target molecule is present in the sample. The smaller porous bead is designed to immobilize magnetic particles. A sample is mixed with magnetic particles and the larger porous bead and allowed to incubate. Then the smaller porous bead is added into the sample mixture and allowed to incubate. The sample mixture is then pumped through the channel [501] in the sensor. The detection volume [301] comprises of an array of posts that are spaced to block the larger porous beads and pass the smaller porous beads. The detection volume [302] serves as a reference of the environment. The net induced voltage from the sample sensor pair [101-102] is proportional to the quantity of magnetic particles immobilized in the detection volume [301]. The net induced voltage from the sample sensor pair [101-102] corresponds to the number of target molecules in the detection volume [301]. The detection volume [303] comprises of an array of posts that are spaced to block the smaller porous beads. The detection volume [304] serves as a reference of the environment. The net induced voltage from the control sensor pair [103-104] is proportional to the quantity of magnetic particles immobilized in detection volume [303].

The sensor may be manufactured on an electrically insulating substrate. The substrate may be made of solid material, flexible material, composite material, laminates, or a combination thereof. The substrate may be silicon with a layer of oxide, silicon with a layer of polymer, FR-4 glass epoxy, or glass.

Figure 4:
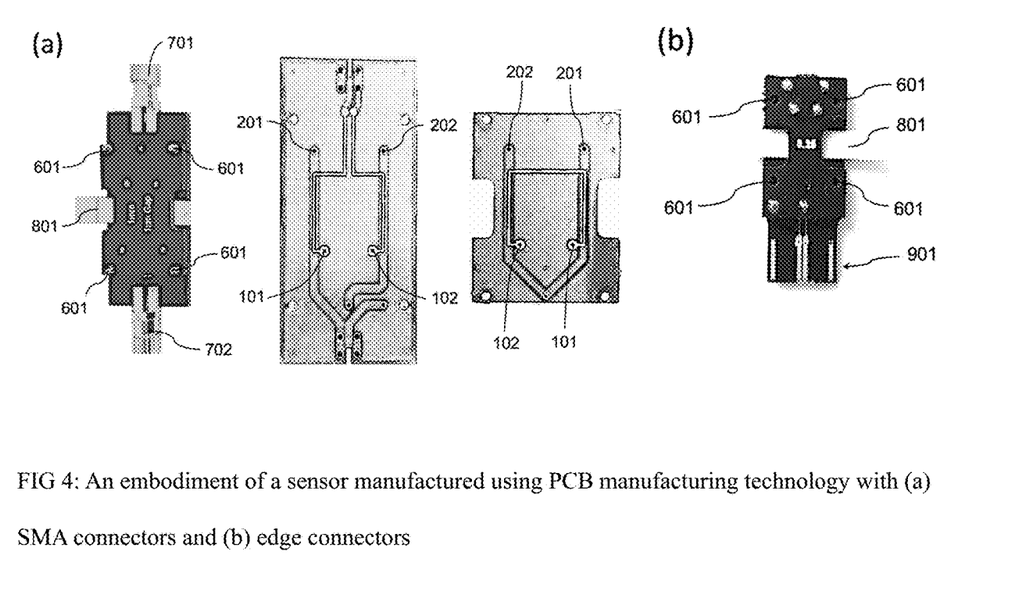
FIG. 4A is a photograph of a PCB embodiment of the sensor with SMC connectors
FIG. 4B is a photograph of a PCB embodiment of the sensor with an edge connector

FIG. 4A is an embodiment of a sensor manufactured using PCB manufacturing technology. The PCB board material used as a substrate is FR-4 glass-reinforced epoxy laminate. The excitation conductors [201] and [202] are coated with an insulating material that is the same color as the PCB board so only the through-holes for interconnecting are readily visible. The sensing conductors [101] and [102] are on top of the excitation conductors [201] and [202] respectively. The two PCB boards are aligned using alignment pins [601]. High precision stainless steel shims are used to set a gap between the two PCB boards to produce the detection volume [301] and [302] which is not visible in FIG. 4A. The alignment pins are soldered to fix the PCB boards in place. SMA connector [701] is soldered onto the PCB to connect the excitation conductors to a power source such as a waveform generation. SMA connector [702] is soldered onto the PCB to connect the sensing conductors to a voltage detector such as a spectrum analyzer. A completed LFA [801] is dragged through the sensor at a controlled velocity as the net induced voltage is recorded over time using a computer that is interacting with the power source and the voltage detector. The net induced voltage record can be analyzed to determine the quantity of magnetic material in the test line and control line of the LFA.

FIG. 4B is an embodiment of the sensor in FIG. 4A wherein the connector is an edge connector [901].

In one embodiment, the power source and voltage detector can be integrated into a reader. As a non-limiting example, the power source is a radio transmitter providing a single frequency voltage signal to power the excitation conductors. The voltage detector is a radio receiver recording the magnitude of the net induced voltage at the transmission frequency. The radio transmitter and receiver can be a system on a chip. The reader may comprise additional electronics to control the transmitter, record data, process data, analyze data and provide a meaningful result to an operator. The meaningful result can be displayed on an LED indicator, a screen or a mobile phone. The user may provide controls to the reader via a touchpad, a screen or a mobile phone.

In one embodiment, the sensor can be integrated into the reader. As a non-limiting example, a chain of tests can be fed through the reader for high throughput analysis and reduced cost. The sensor can be engineered and manufactured to provide higher performance.

In one embodiment, the sensor provides one or more connectors to interface with a reader. The connectors can be USB connectors, edge connectors, SMA connectors, SMC connectors or a means to electrically connect the sensor to a reader. The reader may provide power to the excitation conductors and record the net induced voltage signal from the sensing conductors. The reader may comprise a frequency generator, an amplifier, a low noise amplifier, a demodulator, an analog to digital converter, a microprocessor and a touch screen. The touch screen may provide additional computational power, internet access and/or other services such as a smartphone. A smartphone may provide the function of the reader.

In one embodiment, the excitation conductors may be powered by a voltage waveform. The waveform may be sinusoidal. The waveform may be provided continuously, in short bursts, or any suitable pattern that can excite an informative sensing signal. A special waveform may be provided to exploit the non-linear susceptibility of magnetic particles. The waveform may provide a single frequency or more than one frequency. The waveform may provide a frequency in the range of 10 kHz to 2 GHz. The frequency may be selected to provide a specified sensitivity. The waveform may provide power in a range of 0.1 mW to 10 W. The power may be selected to provide a specified sensitivity. The waveform may provide power continuously or pulsed.

In one embodiment, the sensor signal is recorded electronically. The sensing conductor signal is recorded continuously, periodically, once, or any suitable pattern that can reveal useful information about the sensor or the test. As a non-limiting example, the test can be an LFA. The sensor signal can begin recorded right before a sample is introduced and continue to record until the LFA is dry. As a non-limiting example, the sensor signal may be recorded after the LFA is dry.

In one embodiment, the test can be performed external to the sensor. A completed test can be inserted into the sensor for reading. An LFA can be performed before inserting it into the sensor for reading. The completed LFA can be dragged through the sensor while the sensor is continuously recording the sensing conductor signal. A chain of completed LFA can be dragged through the sensor while the sensor is continuously recording.

The capability of the sensor described in [0041] was evaluated using a standard hCG (pregnancy test) model system based on readily available, well-characterized antibodies. The LFA half-strip was prepared on a Whatman FF80HP nitrocellulose membrane with a Whatman 5CF5 absorbent pad. A BioDot XYZ3060 was used to dispense 1 μg/cm polyclonal anti-α hCG antibody at the test line and 1 μg/cm of anti-mouse antibody at the control line. hCG model protein was diluted in LFA Buffer and 10 μL of each sample was mixed with μL of 200 nm Adembeads functionalized with mouse monoclonal anti-13 hCG, and the 3 mm half-strip was dipped in the mixture. The strips were then washed by adding 40 μL of LFA buffer to the dipping tube. The test line and control line on each strip was characterized using the biosensor. Then, each line was cut from the LFA strip to be measured in an alternating gradient force magnetometer (AGFM) to correlate the biosensor signal with the number of nanoparticles. The signal from a blank sample enables the quantification of non-specific binding.

Figure 5:
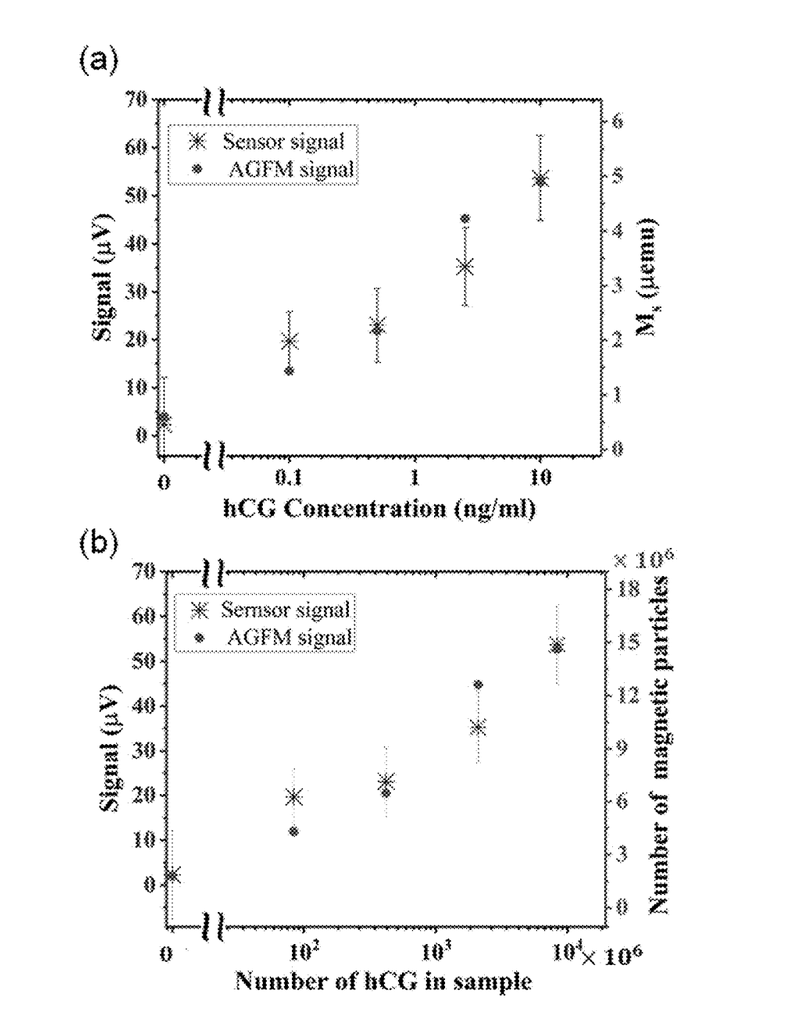
FIG. 5 is a set of graphs comparing the sensor signal and a magnetometer (AGFM) signal of the test line of an LFA for the various concentrations of the hCG pregnancy hormone.

FIG. 5 shows the capabilities of the sensor in [0041] using the LFA in [0049]. The LFA is fed through the sensor at a controlled velocity and the sensor signal is recorded continuously. The peak signal from the sensor is compared with the results of an AGFM. The peak signal from the sensor and AGFM measurements show a close correlation that increases with hCG concentration. The signal for the control sample (hCG concentration of 0 ng/ml) is not zero because some of the magnetic particles (Adembead from Ademtech) are trapped nonspecifically as they flow through the LFA membrane. Significantly, both the sensor and the AGFM can detect the minute amount of magnetic particles nonspecifically bound in the test line of the control sample. The nonspecifically bound magnetic particles in the LFA membrane is below the detection limit of both the sensor and AGFM. This indicates that the quantity of magnetic particles non-specifically bound in the test line of a control sample is larger than the quantity of magnetic particles non-specifically bound to the LFA membrane. The sensor can reliably detect an hCG concentration below 100 pg/ml.

Figure 6:
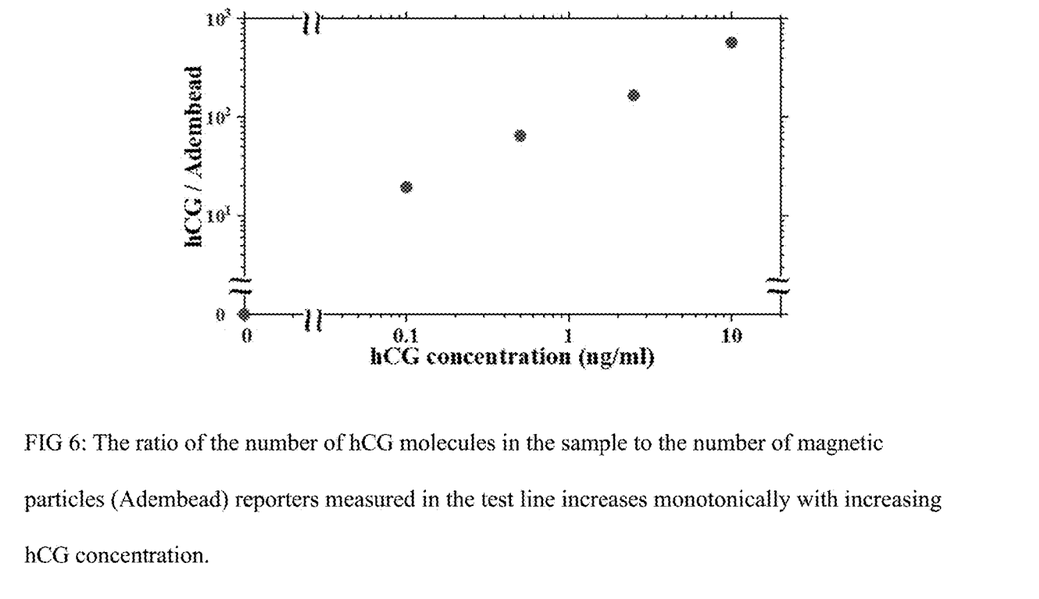
FIG. 6 is a graph showing the ratio of hCG molecules to magnetic particles (Adembead) in the test line of an LFA for the various concentrations of the hCG pregnancy hormone.

FIG. 6 shows a graph comparing the number of hCG molecules present in the test sample versus the number of magnetic particles bound to the test line. On average, this test requires approximately 100 hCG molecules for each magnetic particle immobilized in the test line. The amount of hCG molecules in the sample per magnetic particle found in the test line varies with hCG concentration. The ratio of hCG molecules to the magnetic particles in the test line increases monotonically from approximately 20 at a concentration of 0.1 ng/ml to 500 at 10 ng/ml. The hCG analyte is mixed with the magnetic particles before applying them to the LFA to provide sufficient incubation time. Therefore, the reaction kinetics of the magnetic particles decorated with hCG as it flows through the available binding sites on the test line may be the limiting factor for the test sensitivity.

The sensor can be used to optimize LFA preparation. As discussed in [0050] and [0051], the quantification of magnetic particles in a detection volume provides valuable information about the quantity of a target molecule in the detection volume. Accurate quantification of molecules in a detection volume provides a powerful metric to evaluate the performance of a test.

What is claimed is:
1. An inductive sensor for characterizing a magnetic material in at least one detection volume, comprising:
   a. a set of inductive sensing conductors, comprising a first inductive sensing conductor set and a second inductive sensing conductor set, wherein said conductor sets are fabricated on and sandwiched between two supporting substrates, and wherein the first inductive sensing conductor set and the second inductive sensing conductor set form a sensor pair, b. a set of excitation conductors fabricated on and sandwiched between two supporting substrates, wherein said set of inductive sensing conductors are sandwiched between said set of excitation conductors, and are configured to providing provide a time-varying magnetic field with a frequency in the range of 10 kHz to 2 GHz, and c. wherein said sensor pair is configured to provide a net induced voltage, which is proportional to a disparity in the quantity of magnetic material in detection volume.

2. A system for sensing molecular species comprising:
a. sensor of claim 1, and
b. molecular recognition elements present in said detection volume, and
c. magnetic particles of an average size of less than about 10 micrometers, and
d. molecular recognition elements bound to said particles.

3. The system of claim 2, wherein said molecular recognition elements are selected from the group consisting of antibodies, proteins, nucleic acids, nucleic acid analogs, sugars, organic molecules, inorganic molecules, and combinations thereof.

4. The system of claim 2, wherein the binding between said molecular species and said molecular recognition elements comprises a linker species.

5. The system of claim 2, wherein said magnetic particles interact with said detection volume using said molecular species and said molecular recognition elements and the characteristics of said magnetic particles correspond to the characteristics of said molecular species.

6. The system of claim 5, where said characteristics of said molecular species provide information on the health of a person or an animal.

7. The system of claim 5, where said characteristics of said molecular species provide information on environmental or substance hazards.

8. The system of claim 5, where said characteristics of said molecular species provide information on biological or chemical safety.

9. A device for characterizing magnetic particles with an average size of less than about 10 micrometers in at least one detection volume comprising:
a. a set of printed circuit board sensing conductors, comprising a first printed circuit board sensing conductor and a second circuit board sensing conductor, said set of printed circuit board sensing conductors sandwiching said detection volume, wherein each printed circuit board sensing conductor does not form current loops in the plane of said supporting substrates, and
b. a set of printed circuit board excitation conductors sandwiching sensing conductors, and configured to providing provide a time-varying magnetic field with a frequency in the range of 10 kHz to 2 GHz, wherein each printed circuit board excitation conductor does not form current loops in the plane of said supporting substrates, and
c. wherein the set of printed circuit board sensing conductors is disposed between of the set of printed circuit board excitation conductors, and wherein the first printed circuit board inductive sensing conductor and the second printed circuit board inductive sensing conductor form a sensor pair.

10. The device of claim 9 comprising a delivery medium wherein:
a. said delivery medium is a lateral flow assay membrane or a microfluidic channel, and
b. said delivery medium comprises at least one detection volume, and
c. the induced voltage across sensing conductors provides the quantity of magnetic particles in said detection volume.

11. The system for sensing molecular species comprising:
a. device of claim 10, and
b. molecular recognition elements present in said detection volume, and
c. magnetic particles of an average size of less than about 10 micrometers, and
d. molecular recognition elements bound to said particles.

12. The system of claim 11, wherein said molecular recognition elements are selected from the group consisting of antibodies, proteins, nucleic acids, nucleic acid analogs, sugars, organic molecules, inorganic molecules, and combinations thereof.

13. The system of claim 11, wherein the binding between said molecular species and said molecular recognition elements comprises a linker species.

14. The system of claim 11, wherein said delivery medium comprises a test and reference detection volumes.

15. The system of claim 11, wherein said delivery medium comprises a control and a reference detection volumes, wherein the net induced voltage across said control and said reference volumes validates device functionality.

16. The system of claim 11, wherein said magnetic particles interact with said detection volume using said molecular species and said molecular recognition elements and the characteristics of said magnetic particles correspond to the characteristics of said molecular species.

17. The system of claim 16, where said characteristics of said molecular species provide information on the health of a person or an animal.

18. The system of claim 16, where said characteristics of said molecular species provide information on environmental or substance hazard.

19. The system of claim 16, where said characteristics of said molecular species provide information on biological, food or chemical safety.

* * * * *